(12) United States Patent
Yamaguchi

(10) Patent No.: US 6,864,979 B2
(45) Date of Patent: Mar. 8, 2005

(54) PARTICLE SIZE DISTRIBUTION MEASURING APPARATUS

(75) Inventor: Tetsuji Yamaguchi, Kyoto (JP)

(73) Assignee: Horiba, Ltd, Kyoto (JP)

( * ) Notice: Subject to any disclaimer, the term of this patent is extended or adjusted under 35 U.S.C. 154(b) by 123 days.

(21) Appl. No.: 10/010,595

(22) Filed: Dec. 5, 2001

(65) Prior Publication Data

US 2002/0071119 A1 Jun. 13, 2002

(30) Foreign Application Priority Data

Dec. 8, 2000 (JP) .................................... 2000-374996
Dec. 15, 2000 (JP) .................................... 2000-381313

(51) Int. Cl.$^7$ ................................................ G01N 15/02
(52) U.S. Cl. ...................................... 356/336; 356/338
(58) Field of Search .............................. 356/335–343, 356/244, 246, 440, 39; 250/574, 575; 73/865.5

(56) References Cited

U.S. PATENT DOCUMENTS

| | | | | |
|---|---|---|---|---|
| 3,225,601 A | * | 12/1965 | Derek | 356/246 |
| 3,419,722 A | * | 12/1968 | Meikle | 250/576 |
| 3,582,222 A | * | 6/1971 | Hoblik | 356/246 |
| 3,734,601 A | * | 5/1973 | Heiss | 356/246 |
| 3,867,042 A | * | 2/1975 | Mayer et al. | 356/246 |
| 3,961,899 A | * | 6/1976 | Trivedi et al. | 422/102 |
| 4,367,043 A | * | 1/1983 | Sweet et al. | 356/338 |
| 4,762,413 A | | 8/1988 | Namba et al. | |
| 4,781,460 A | | 11/1988 | Bott | |
| 4,794,806 A | * | 1/1989 | Nicoli et al. | 73/863.01 |
| 4,828,388 A | | 5/1989 | Namba | |
| 5,134,445 A | * | 7/1992 | Toge | 356/336 |
| 5,182,617 A | * | 1/1993 | Yoneyama et al. | 356/440 |
| 5,247,558 A | * | 9/1993 | Hendrix et al. | 378/51 |
| 5,428,443 A | * | 6/1995 | Kitamura et al. | 356/336 |
| 5,456,102 A | * | 10/1995 | Moorehead | 73/1.24 |
| 5,471,298 A | | 11/1995 | Moriya | |
| 5,684,583 A | | 11/1997 | Abe et al. | |
| 5,956,139 A | | 9/1999 | Meyer et al. | |
| 6,091,492 A | | 7/2000 | Strickland et al. | |
| 6,310,356 B1 | * | 10/2001 | Yuhara et al. | 250/574 |
| 6,389,912 B1 | * | 5/2002 | Wood | 73/865.5 |
| 6,458,267 B2 | * | 10/2002 | Kaendler | 210/85 |
| 6,473,177 B2 | | 10/2002 | Yamaguchi | |
| 2003/0110854 A1 | * | 6/2003 | Nakada et al. | 73/204.22 |

FOREIGN PATENT DOCUMENTS

| | | |
|---|---|---|
| JP | 61-178643 | 8/1986 |
| JP | 2-285238 | * 11/1990 |
| JP | 05-113396 | 5/1993 |

* cited by examiner

*Primary Examiner*—Hoa Q. Pham
(74) *Attorney, Agent, or Firm*—Brown Raysman Millstein Felder & Steiner LLP

(57) ABSTRACT

The present application provides a method of operating a particle size distribution measuring apparatus sample solution circulation system is constructed so as to reverse a flow direction of a sample solution which flows through a flow cell prior to a measurement of the particle size distribution within the sample solution.

4 Claims, 3 Drawing Sheets

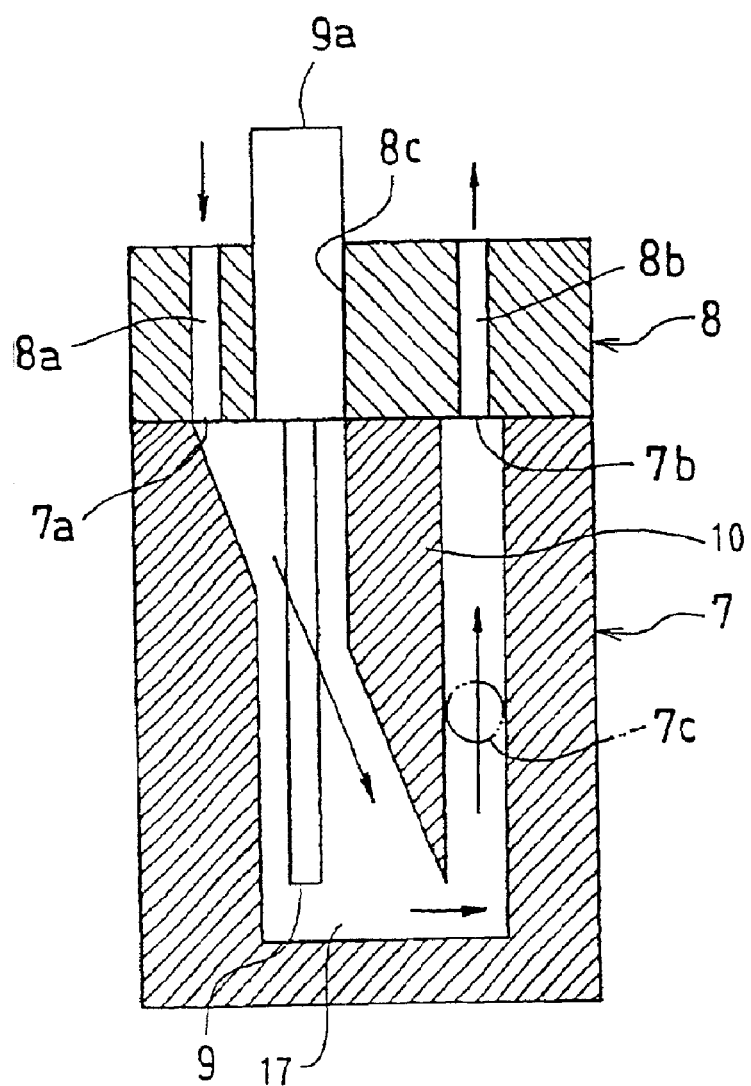
F I G. 2

PARTICLE SIZE DISTRIBUTION MEASURING APPARATUS

FIELD OF THE INVENTION

The present invention relates to a particle size distribution measuring apparatus.

DESCRIPTION OF THE PRIOR ART

There are currently a number of particle size distribution measuring systems available. For example, one conventional particle size distribution measuring apparatus comprises an irradiating part, a flow cell provided within a flow path, and a detector. The flow cell includes a sample solution flow therein. Commonly, the flow cell includes and inlet port and an outlet port on a top and a bottom surfaces of the cell. The irradiating part emits laser light and irradiates the flow cell and the sample solution flow contained therein. The detector detects the laser light emanating from the irradiating part and light scattered by particles within the sample solution.

However, one shortcoming of the above-described conventional particle size distribution measuring apparatus relates to the spillage of the sample solution. On occasion, a soiled flow cell and holder will be detached from the flow path for washing. Frequently, sample solution remaining in the flow cell is spilled from the port provided on the bottom surface of the cell when detaching the flow cell from the flow path. The sample solution may comprise a strong acid, alkali solution, or organic solvent. Therefore the spillage of the sample solution as described above could result in an accident or a hazardous condition.

The present invention has been invented considering the matter described above, and it is an object of the present invention to provide a particle size distribution measuring apparatus in which the sample solution circulates fluently in the flow cell. Furthermore, it is an object of the present invention to provide an apparatus wherein the flow cell may be detached from the flow path without spilling the sample solution, and further permit the flow cell to be washed easily and surely.

Another conventional particle size distribution measuring apparatus currently available includes an irradiating source capable of emitting laser light, a measuring part in fluid communication with a flow path, a pump for circulating the fluid through the flow path, and a detector. The measuring part includes a flow cell capable of flowing a sample solution. The pump is in communication with a supplying part which supplies the sample solution to the flow path. The pump circulates a the sample solution through the flow path. A draining part for draining the sample solution in the flow path may also be included. The measuring part is used for determining the particle size distribution of the particles in the sample solution.

In the conventional particle size distribution measuring apparatus described above air bubbles may adhered to the surface of the flow cell causing an error in measuring the particle size distribution. As a result, the system is constructed to push the air bubbles out of the flow cell by making the flow velocity of the sample solution in the flow path higher than the usual circulation before the measurement was carried out.

However, in the conventional particle size distribution measuring apparatus constructed as described above, when a diameter of a tube forming the flow path was relatively small, the removal of air bubbles in the flow cell may be insufficient and therefore the degree of measuring accuracy is lowered since the flow velocity of the sample solution is not large enough due to a restriction of the velocity of the sample solution flow in the tube.

The present invention has been invented considering the matter described above, and it is an object of the present invention to provide the particle size distribution measuring apparatus capable of enhancing the degree of measuring accuracy irrespective of a diameter of a tube forming the flow path.

SUMMARY OF THE INVENTION

In order to achieve the above object, the present invention provides a particle size distribution measuring apparatus having an irradiating part which emits laser light, a flow cell provided within a flow path which is incident to the laser light and through which a sample solution flows, and a detector for detecting light from the irradiating part and scattered by particles in the sample solution. The flow cell includes two ports to be an inlet and an outlet for the sample solution, positioned on a top surface of the cell, wherein a separating element is provided between the two ports of the flow cell in a downward direction. The separating element is positioned within the flow cell in such a way that the sample solution introduced from either one of the two ports into the flow cell is guided out of another port through the vicinity of the flow cell bottom. In addition, the lower section of the separating element has an inclined surface so as to decrease in width toward a bottom end.

The present invention circulates the sample solution fluently through the flow cell. In addition, the present invention allows the flow cell to be detached from the flow path without spilling the sample solution, thereby providing a flow cell of a particle size distribution measuring apparatus capable of being washed easily and surely.

In another embodiment, the present invention provides a particle size distribution measuring apparatus being comprising a pump for circulating a sample solution, a flow cell in the flow path through which the sample solution circulates, an irradiating part which emits laser light incident on the flow cell, and a detector for detecting light from the irradiating part and light scattered by particles in the sample solution contained within the flow cell. The sample solution circulation system is constructed so as to reverse the flow direction of the sample solution, which flows through the flow cell prior to a measurement of the particle size distribution performed by irradiating laser light on to the flow cell from the irradiating part.

The present invention provides a particle size distribution measuring apparatus capable of removing air bubbles in the flow cell irrespective of a diameter of a tube forming the flow path, thereby enhancing the degree of measuring accuracy.

BRIEF DESCRIPTION OF THE DRAWINGS

FIG. 2 is an illustration showing schematically a constitution of a flow cell in the above-mentioned embodiment.

DETAILED DESCRIPTION OF THE PREFERRED EMBODIMENTS

Hereinafter, an embodiment of the present invention will be described referring to the accompanying drawings.

Figure 1:
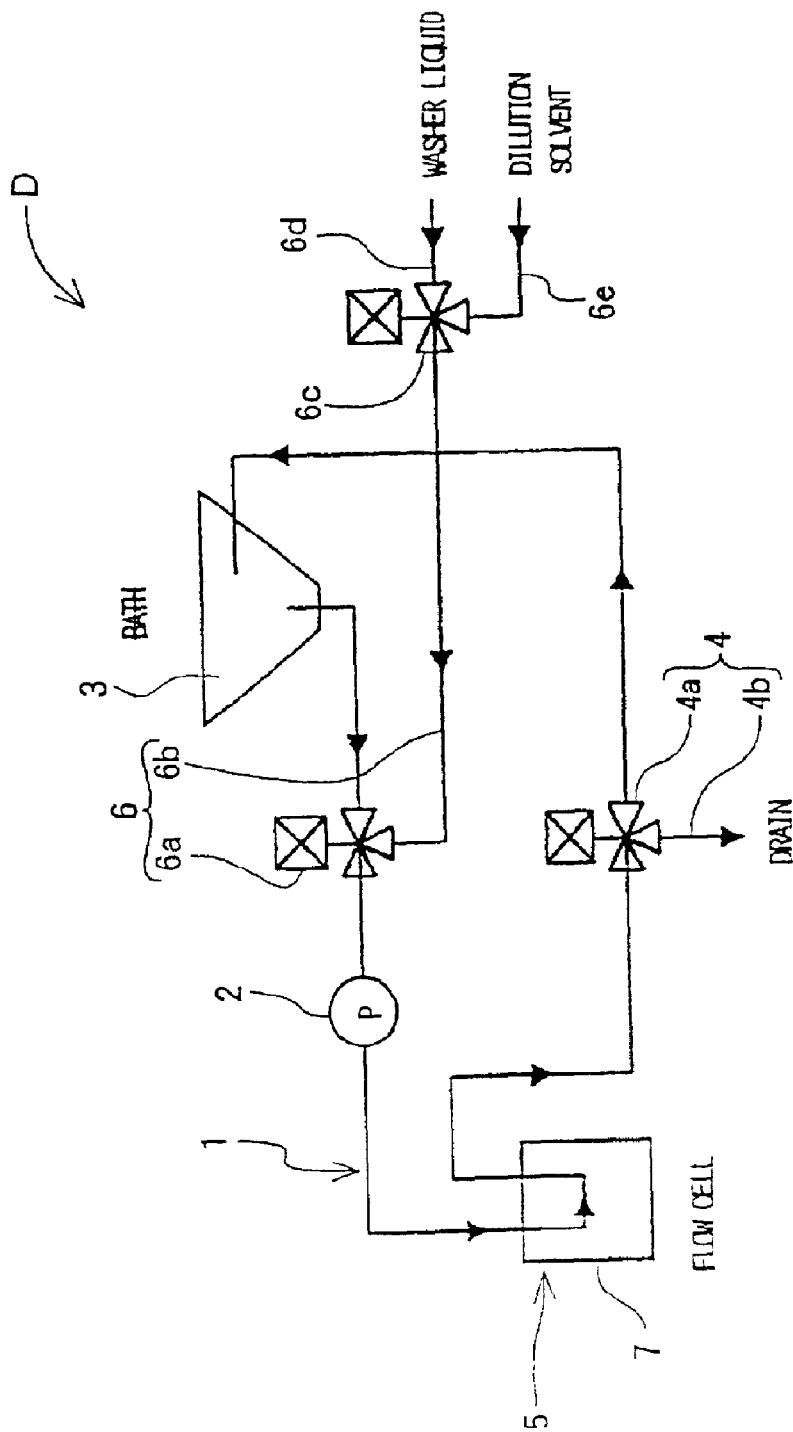
FIG. 1 is an illustration showing schematically a constitution of a particle size distribution measuring apparatus according to one embodiment of the present invention.

FIG. 1 is an illustration showing schematically a particle size distribution measuring apparatus according to one embodiment of the present invention.

The particle size distribution measuring apparatus D comprises a flow path 1 through which a sample solution (not shown) containing sample particles to be measured dispersed within the sample solution (not shown) circulates, a pump 2 for circulating the sample solution, a supplying part 3 for supplying the sample solution to the flow path 1, a draining part 4 for draining the sample solution in the flow path 1, a measuring part 5 for determining the particle size distribution of the sample particles in the sample solution, and an injecting part 6 for injecting a dilution liquid 6e (for example, water) for diluting the sample solution and a washer liquid 6d used for washing the inside of the flow path 1 into the flow path 1. Those skilled in the art will appreciate that the present invention is not limited to the configuration described above, and the configuration of the present invention may be appropriately set.

The particle size distribution measuring apparatus D is a dynamic light scattering type particle size distribution measuring apparatus, in which laser light is used to irradiate sample particles dispersed in the sample solution and the particle size distribution is determined from the frequency intensity distribution of the light scattered by the sample particles disbursed within a sample solution. In short, the present system is constructed based on the so-called dynamic light scattering theory. However, the particle size distribution measuring apparatus D of the present invention is not limited to the particle size distribution measuring apparatus using dynamic light scattering theory.

Exemplary sample solutions may include sample particles, including, without limitation, a solution formed by diluting organic pigments, ceramic, abrasives for a semiconductor wafer and a hard disk, or ink for an ink-jet printer with an appropriate dispersant (water, alcohol such as ethanol and the like).

FIG. 1 shows the flow path 1, the supplying part 3, the injecting part 6, the pump 2, the measuring part 5 and the draining part 4, which are described above, provided in a predetermined order. The order of the individual components of the present invention not limited to that described above, and it may be appropriately set.

The pump 2 is constructed so as to be capable of three states: a normal first rotation, a stop, and a reverse second rotation. When the pump 2 is in the state of the normal rotation the circulation of the sample solution in the flow path 1 becomes a first circulation in which the sample solution passes through the supplying part 3, the injecting part 6, the pump 2, the measuring part 5, and the draining part 4 in this order. Thereafter, the sample solution then flows towards the supplying part 3. When the pump 2 is in the state of the reverse rotation the circulation of the sample solution in the flow path 1 becomes a second circulation in which the sample solution passes through the supplying part 3, the draining part 4, the measuring part 5, the pump 2 and the injecting part 6 and then flows again toward the supplying part 3. The circulation of the sample solution in the flow path 1 may be stopped by bringing the pump 2 to the state of the stop.

The supplying part 3 may comprise, for example, a dispersing bath having a charging opening (not shown) for charging the sample solution into the inside thereof. In an alternate embodiment, a dispersing means for dispersing or agitating the sample particles in the sample solution contained within the supplying part 3 may be installed. As such, the dispersing means may comprise an ultrasonic bath capable of ultrasonic dispersing, which disperses the sample particles in the sample solution within the supplying part 3. An alternate dispensing means capable of applying an appropriate impact to the supplying part 3 may be used.

The draining part 4 comprises a three-way electromagnetic valve 4a and a draining path 4b. The draining path 4b is connected to the flow path 1 through the three-way electromagnetic valve 4a, and enables the draining of the sample solution from the flow path 1. The draining part 4 of the present invention enables draining the sample solution flowing through the flow path 1 from the draining path 4b by switching the three-way electromagnetic valve 4a. Further, the configuration of the draining part 4 is not limited to that described above, and may include, for example, a two two-way electromagnetic valve (not shown) instead of the three-way electromagnetic valve 4a shown in FIG. 1. If using two two-way electromagnetic valves one two-way electromagnetic valve may be installed at the draining path 4b and another two-way electromagnetic valve may be installed in the flow path 1.

The measuring part 5 has a flow cell 7 capable of flowing the sample solution and permitting the irradiating part (not shown) to irradiate the sample solution with the flow cell 7 with laser light. A detector (not shown) may be for detecting the light scattered by sample particles in the sample solution contained in the flow cell 7.

Figure 3:
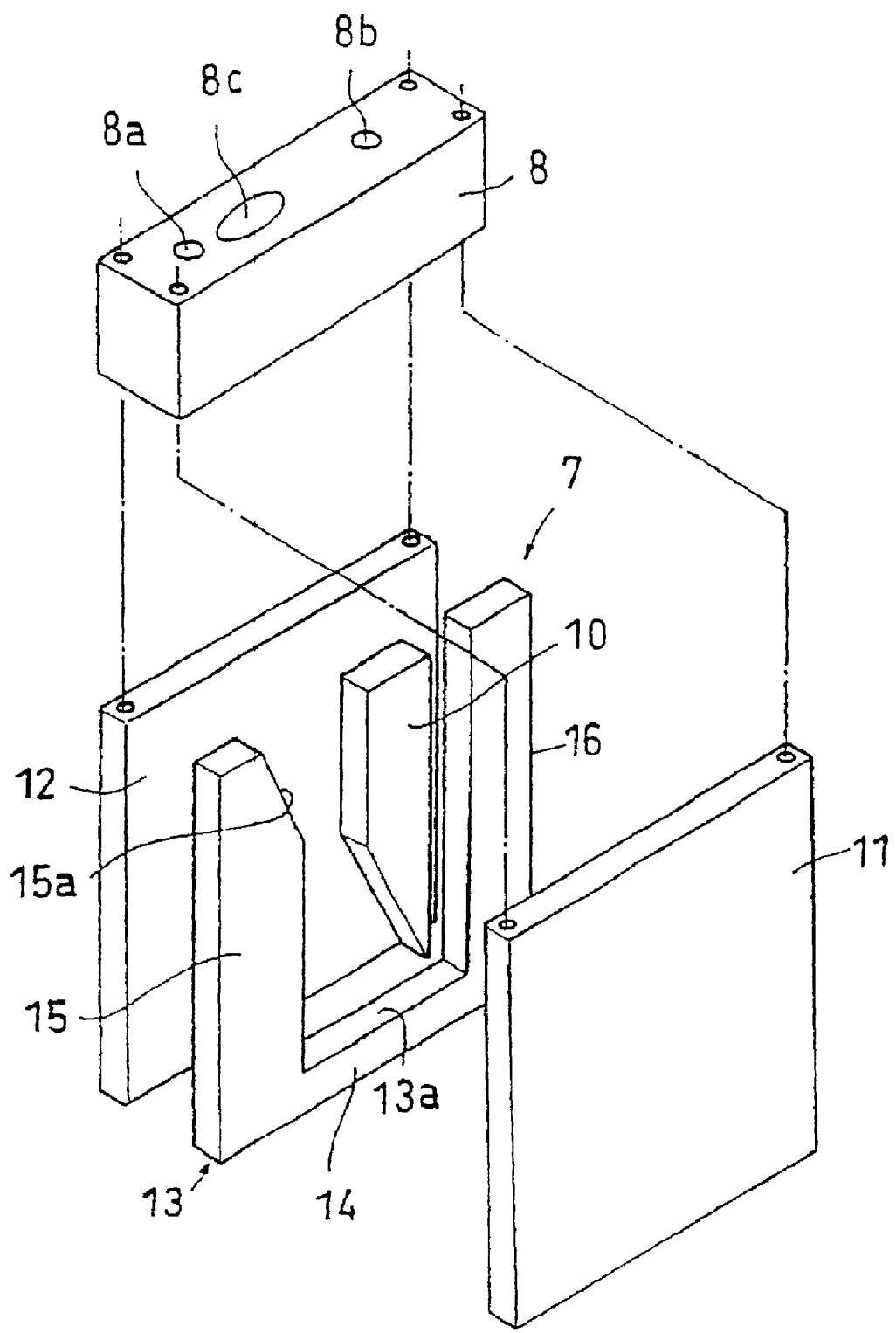
FIG. 3 is an exploded perspective view showing schematically the constitution of the flow cell in the above-mentioned embodiment.

FIG. 2 and FIG. 3 are several views of the present invention showing schematically the constitution of the flow cell 7.

As shown in FIG. 2, the flow cell 7 is formed using a material (for example, glass) through which laser light from the irradiating part transmits, and is set in the flow path 1 together with a lid 8 of the cell secured freely removably on the flow cell 7 in a state of being retained by a cell-holder (not shown).

The flow cell 7 and the lid 8 of the cell are constructed in such a way that these parts, the flow cell 7 and the lid 8 may hold a thermometer 9 in a state of being inserted into the flow cell 7.

The flow cell 7 is provided with two ports 7a, 7b to be an inlet and an outlet of the sample solution on a top surface of the cell and a separating element 10 is provided from a position between the two ports 7a, 7b of the flow cell 7 in a downward direction in such a way that the sample solution introduced from either one of the two ports 7a, 7b into the flow cell 7 is guided out of another port through the vicinity of the bottom of the flow cell 7.

As shown in FIG. 13, the flow cell 7 has a configuration in which a flow path forming element 13 having a cut out section 13a and the separating element 10, which has the identical thickness with the flow path forming element 13, located within the recessed section 13a are sandwiched between two plate elements 11, 12.

The two plate elements 11, 12 have a shape and a size about similar to each other, and are formed so as to be about rectangular in a plan view and about uniform in thickness of any portion.

The flow path forming element 13 has an approximately U-shaped configuration which is formed by providing a plate element approximately identical with the two plate elements 11, 12 in height and horizontal width. The cut out section 13a extends from the upper central section of the plate element toward the bottom, and is composed of a bottom wall section 14, a left wall section 15 and a right wall section 16, which are installed consecutively from both ends of the bottom wall section 14 upward. The top surface of the bottom wall section 14 is approximately horizontal plane.

The upper section 15a of the inner surface, the surface opposed to the right wall section 16 of the left wall section 15, is an inclined surface in which the lower section is closer to the opposed right wall section 16, and the section between the middle and the bottom of the inner surface, the surface opposed to the right wall section 16 of the left wall section 15, is approximately perpendicular surface 16. The inner surface, the surface opposed to the left wall section 15 of the right wall section 16, is the approximately perpendicular surface.

The separating element 10 is located in such a way that the top surface thereof is in the same plane as the plane including the top surface. More specifically, the top surface of the separating element 10 is aligned with the top surface of the left wall section 15 and the top surface of the right wall section 16 of the flow path forming element 13. The surface of the separating element 10, which is on the side opposed to the right wall section 16, is approximately perpendicular to the surface of the right wall section 16. The upper surface of the separating element 10, which is on the side opposed to the left wall section 15, is the approximately perpendicular to the middle section of the left wall section 15. The lower surface of the separating element 10 is inclined and decreases as it approaches the right wall section 16 toward the bottom. More specifically, the separating element 10 decreases in width from the middle section toward the bottom and has a pointed-shape in a longitudinal section.

The top surface of the flow cell 7 constructed as described above, includes ports 7a, 7b which is surrounded with the top surface of the left wall section 15 and the right wall section 16 of the flow path forming element 13. The top surface of the separating element 10 and the top surfaces of the two plate elements 11, 12, respectively, additionally form the inlet to and the ports 7a, 7b.

When the pump 2 is in a normal rotation, the ports 7a and 7b become an injection port and an ejection port, respectively, of the sample solution at the flow cell 7, and when the pump 2 is in a reverse rotation, the ports 7a and 7b become the ejection port and the injection port, respectively, of the sample solution at the flow cell 7.

Also, in flow cell 7, there is formed a passage 17, which is surrounded with the two plate elements 11, 12, the flow path forming element 13, and the separating element 10. The passage 17 defines a space through which the sample solution passes. The passage 17 is one in which the respective spaces formed from the respective ports 7a, 7b toward the bottom of the flow cell 7 are in communication with each other in the vicinity of the bottom of the flow cell 7, and is approximately U-shaped or V-shaped in a longitudinal section.

The lid 8 of the flow cell 7 may be manufactured from a plurality of materials depending on the properties of the sample solution. For example, a corrosive resistant material such as Teflon, may be used when the sample solution possesses corrosive properties. The lid 8 comprises two connecting paths 8a, 8b, which connect to the two ports 7a, 7b, and an insertion hole 8c for holding or securing a thermometer 9 inserted into the port 7a on one side into the flow cell 7. Further, O-ring and piping fittings (not shown) may be built into the connecting paths 8a, 8b. These O-ring and piping fittings may also be formed using a material similar to the lid 8 of the flow cell 7.

The thermometer 9 measures the temperature of the sample solution when submerged in the sample solution within the flow cell 7. The thermometer 9 is built into a shield tube 9a of stainless steel or similar material having the form of an extremely thin rod, and is secured to the lid 8 of the flow cell 7 using a seal means (for example, O-ring) and a securing means (for example, screw). The thermometer 9 is located at a position which does not interfere the laser light from the irradiating part emitting laser light incident with the flow cell 7.

The shield tube 9a comprises a section inserted into the flow cell 7 having a relatively small diameter, and a section inserted into the lid 8 of the cell and projecting above the lid 8 of the flow cell 7 having a relatively large diameter.

The flow cell 7, having the lid 8 attached thereto and the thermometer 9 retained thereby, are set in the flow path 1. In measuring the particle size distribution, laser light from the irradiating part is directed to the appropriate measuring location 7c of the flow cell 7. Thereafter, the resulting scattered light from the sample particles in the sample solution is detected by the detector, and the particle size distribution is measured. The temperature of the sample solution measured by the thermometer 9 is inputted into a computing process for measuring the particle size distribution. Those skilled in the art will appreciate that the measuring location 7c irradiated with laser light is set to about the midsection of the distance from the port 7b between of the passage 17 to the bottom of the flow cell 7, and the passage 17 extends approximately linearly and perpendicularly from the port 7b up to the bottom of the flow cell 7, and further is formed in such a way that the cross-sectional area of the passage 17 is approximately constant over the passage.

While the measuring location 7c irradiated with laser light is set to about the midsection of the distance from the port 7b, the thermometer 9 is inserted into the flow cell 7 from the other port 7a and positioned to measure the temperature of the sample solution at the vicinity of the bottom of the flow cell 7. The thermometer 9 is positioned within the flow cell 7 so as not produce reflected light and scattered the laser light irradiated to the measuring location 7c, which lower the accuracy of measuring, and will not affect the measurements of the particle size distribution. Those skilled in the art will appreciate that it becomes possible to measure the temperature of the sample solution more accurately by the thermometer 9 by making the measuring location 7c irradiated with laser light approach the bottom of the flow cell 7.

The injecting part 6 comprises a three-way electromagnetic valve 6a and an injecting path 6b, which is connected to the flow path 1 through the medium of the three-way electromagnetic valve 6a. The injector path 6b is used for injecting disjunctively the washer liquid or the dilution liquid into the flow path 1. A three-way electromagnetic valve 6c is installed upstream of the injecting path 6b, and a washer liquid supplying path 6d for supplying the washer liquid and a dilution liquid supplying path 6e for supplying the dilution liquid are connected to the three-way electromagnetic valve 6c.

In the injecting part 6 constructed as described above, it is possible to inject disjunctively the washer liquid or the dilution liquid into the flow path 1 by switching the three-way electromagnetic valves 6a, 6c appropriately. Further, the configuration of the injecting part 6 is not limited to that described above, and may include, for example, two two-way electromagnetic valves, which may be used in place of the three-way electromagnetic valve 6a. If using a two two-way valve system, one two-way electromagnetic valve may be installed at the injecting path 6b and another two-way electromagnetic valve may be installed in the flow path 1. An alternate embodiment of the two two-way valve system uses one two-way electromagnetic valve installed at the washer liquid supplying path 6d and another two-way electromagnetic valve installed at the dilution liquid supplying path 6e.

The present invention discloses the operation of the particle size distribution measuring apparatus D constructed as described above. In order to measure sample particles disbursed in a sample solution using the particle size distribution measuring apparatus D, first, the sample solution to be measured is supplied from the supplying part 3 into the flow path 1. Thereafter, the sample solution is circulated in the normal direction in the flow path 1 by bringing the pump 2 to the state of normal rotation. When the sample solution circulating through the flow path 1 is required for dilution, the dilution liquid may be injected in an appropriate amount from the injecting part 6.

After the sample solution is circulated in a first direction for a given period of time, the pump 2 is brought to the state of the stop, and then to the state of the reverse rotation. Thereafter, the sample solution comes to circulate through the flow path 1 in a second direction opposite the first direction. After the sample solution is reversely circulated for a given period of time, the sample solution circulating in the flow cell 7 of the measuring part 5 is stopped by bringing the pump 2 to the state of the stop, and then the measurement of the sample particles disbursed within the sample solution is performed at the measuring part 5 by the way described above.

In a convention particle size distribution measuring apparatus, the adherence of air bubbles to the inner wall of a flow cell will cause the laser light from the irradiating part to scatter similarly to the sample particles, thus resulting in a deterioration in the accuracy of measuring. Those skilled in the art will appreciate that the particle size distribution measuring apparatus D of the present invention moves the sample solution in multiple directions, and by reversing the flow of the sample solution which flows through the flow cell 7 prior to the measurement as described above, imparts a force to the air bubbles adhered to the inner wall of the flow cell 7. As a result, the air bubbles are removed. Therefore, when laser light is irradiated from the irradiating part, the detector detects only the light scattered by the sample particles suspended on the surface of the inner wall of the flow cell 7 without scattering of laser light by the air bubbles adhered to the inner wall of the flow cell 7.

To enhance the effect of removing the air bubbles, the sequential normal/reverse operation, which changes the sample solution circulating normally through the flow path 1 to the reverse circulation by bringing the pump 2 to the state of the stop from the state of the normal rotation and then by bringing the pump 2 to the state of the stop after bringing to the state of the reverse rotation, may be performed not only one time but may be repeated several times as desired. In this case, the sample solution in the flow path 1 also comes to repeat the circulation in the first and second directions alternately, thereby permitting the removal of air bubbles strongly adhering to the inside of the flow cell 7.

In the above-mentioned sequential normal/reverse operation, the amount of time the pump 2 operates in the states of the normal rotation, stops, and operates in the reverse rotation may also be appropriately adjusted depending on the conditions such as the viscosity of the sample solution. For example, when the sample solution is ethylene glycol, a material with a viscosity nearly twenty times higher than that of water, the velocity of flow of the sample solution in the piping and the flow path 1 becomes low. However, it is possible to sufficiently attain the effect of removing the air bubbles in the flow cell 7 when the periods of time in which the pump 2 is in the state of the normal rotation and the reverse rotation are set to a long period to ensure the sample solution is circulated normally and reversely through the flow path 1.

It may be desirable to shorten a period of time allowed for the pump 2 to be in the state of the stop before the pump 2 is reversed from the state of the normal rotation to the state of the reverse rotation. Alternately, it may be desirable to perform rapid and instantaneous switching between the states of the normal rotation, stop, and reverse rotation of the pump 2. The shaking of the air bubbles in the flow cell 7 becomes more effective by operating the particle size distribution measuring apparatus D as described above, and removal efficiency of the air bubbles is increased.

Once a given measurement at the measuring part 5 is completed, the sample solution in the flow path 1 becomes unnecessary. The present invention permits the sample solution in the flow path 1 to be drained from the draining part 4. It may be necessary to wash the inside of the flow path 1 following a measurement. A washer liquid may be injected from the injecting part 6 into the flow path 1 following the measurement and circulated through the flow path 1 by the pump 2. Thereafter, the spent washer liquid may be drained from the draining part 4 once washing is completed. Those skilled in the art will appreciate that the washing effect may be enhanced by sequentially alternating between normal circulation and reverse circulation as described above.

Even though the inside of the flow path 1 may be washed as described above, it may be extremely difficult to completely prevent the inner wall of the flow cell 7 from being fouled with bilge and the like. Therefore, conventionally, the flow cell 7 has been cleaned by detaching the flow cell 7 from the flow path 1 and scrubbing away the fouling in the flow cell 7 with the cleaning member such as a swab or a brush. Those skilled in the art will appreciate that the particle size distribution measuring apparatus D of the present invention, including the flow cell 7, may be washed easily and surely. The lower section of the separating element 10 has an inclined surface which decreases in width toward the bottom end. Therefore, it is possible to scrub the bottom of the flow cell 7 directly, even when the cleaning member such as a swab or brush is inserted through either ports 7a or port 7b. The inclined surface formed on the upper section 15a of the inner surface of the left wall section 15 does not to interfere with the cleaning operation when inserting the cleaning member through the port 7a. The cleaning member may be positioned in the vicinity of the lower section of the separating element 10, and may clean the passage 17 formed on the bottom of the flow cell 7.

Further, it is possible to forcefully scrub not only the bottom of the flow cell 7, but also any locations on the outer surface of the separating element 10 and location one the inner surface of the flow path forming element 13, which forms the passage 17 provided inside thereof.

In the flow cell 7 described above, the sample solution remaining within the flow cell 7 is not spilled when detaching the flow cell 7 from the flow path 1. Since both of ports 7a, 7b are formed on the top surface of the flow cell 7 the likelihood of accidental spillage is reduced or eliminated.

In addition, the flow cell 7 includes a separating element 10. Therefore, the sample solution in the flow cell 7 may be circulated or efficiently and fluently replaced. Therefore, the sample solution introduced into the flow cell 7 from either one of the two ports 7a, 7b and is guided by the separating element 10 out the other port, resulting in a reduced amount of sample solution in the flow cell 7 when compared with the systems not including the separating element 10.

The particle size distribution measuring apparatus D including the flow cell 7 constructed as described above enables the temperature of the sample solution in the vicinity of the location 7c, which is irradiated with laser light, to be measured by the thermometer 9. Therefore, it is possible to allow the measurement of the particle size distribution to reflect more accurately the temperature of the sample solution, which enhances the absolute precision of measurements of the particle size distribution.

In addition, the particle size distribution measuring apparatus D described above may remove air bubbles positioned within the flow cell 7, without a limitation to the diameter of the tube forming the flow path 1, thereby enhancing the degree of measuring accuracy of the system. Since the removal of the air bubbles in the flow cell 7 may be done surely, it is not necessary to check whether the air bubbles have adhered to the inner wall of the flow cell 7. Those skilled in the art will appreciate that the particle size distribution measuring apparatus D is well suited for performing a series of steps including supplying the sample solution to the flow path 1, measuring the particle size distribution of the sample solution, and washing the inside of the flow path 1 upon completion. In addition, the process described above may be repeated and designed for automatic or unattended operation.

Those skilled in the art will appreciate that the present invention may be constructed wherein the capability to retain the thermometer 9 is eliminated, thereby circulating replacing the sample solution more efficiently and fluently. In addition, as described above, the flow cell 7 of the present invention may be detached without spilling the sample solution therefrom, and may be washed easily and surely.

The present invention provides a particle size distribution measuring apparatus D capable of removing air bubbles in the flow cell to enhance the degree of measuring accuracy irrespective of a diameter of a tube forming the flow path.

What is claimed is:

1. A method of operating a particle size distribution measuring apparatus, comprising;

providing a particle size distribution measuring apparatus comprising a flow path having a flow cell in fluid communication with a pump;

circulating a sample solution in a first direction through the flow path;

stopping the circulation of the sample solution in the first direction;

circulating the sample solution in a second direction through the flow path;

stopping the circulation of the sample solution in the second direction;

irradiating the sample solution within flow cell with laser light;

calculating a particle size distribution of the sample solution by detecting light scattered by particles within the sample solution.

2. The method of claim 1 further comprising injecting a diluting liquid into the sample solution prior to circulating the sample solution in a first direction through the flow path.

3. The method of claim 1 further comprising calculating the particle size distribution using dynamic light scattering theory.

4. A method of operating a particle size distribution measuring apparatus, comprising;

injecting a diluting liquid into a sample solution located within a particle size distribution measuring apparatus;

circulating the sample solution through the particle size distribution measuring apparatus in a first direction;

terminating the circulation of the sample solution through the particle size distribution measuring apparatus;

circulating the sample solution through the particle size distribution measuring apparatus in a second direction;

terminating the circulation of the sample solution through the particle size distribution measuring apparatus; and irradiating the sample solution located within the particle size distribution measuring apparatus with laser light; and measuring the particle size distribution within the sample solution using dynamic light scattering theory.

* * * * *